US00PP21790P2

(12) United States Plant Patent
van den Aardwegh

(10) Patent No.: US PP21,790 P2
(45) Date of Patent: Mar. 15, 2011

(54) ***ECHINACEA* PLANT NAMED 'WHITE MIST'**
(50) Latin Name: *Echinacea hybrida*
Varietal Denomination: White Mist

(76) Inventor: Cornelis Marinus van den Aardwegh, Hillegom (NL)

( * ) Notice: Subject to any disclaimer, the term of this patent is extended or adjusted under 35 U.S.C. 154(b) by 0 days.

(21) Appl. No.: 12/592,666

(22) Filed: Dec. 1, 2009

(51) Int. Cl.
*A01H 5/00* (2006.01)

(52) U.S. Cl. ..... Plt./428

(58) Field of Classification Search ..... Plt./263, Plt./428

See application file for complete search history.

*Primary Examiner*—Susan B McCormick Ewoldt
(74) *Attorney, Agent, or Firm*—Audrey Charles

(57) ABSTRACT

A new and distinct cultivar of *Echinacea* plant named 'White Mist', particularly distinguished by white-colored ray florets, floriferous, compact habit, healthy, abundant foliage, and good mildew resistance, is disclosed.

1 Drawing Sheet

Latin name of genus and species of plant claimed: *Echinacea hybrida.*

Variety denomination: 'White Mist'.

BACKGROUND OF THE INVENTION

The present invention relates to a new and distinct cultivar of *Echinacea* plant botanically known as *Echinacea hybrida* and hereinafter referred to by the cultivar name 'White Mist'. The new cultivar originated from an open pollination in 2005 in a nursery location in Hillegom, The Netherlands between unknown male and female *Echinacea* plants. The nursery location was densely populated with *Echinacea purpurea, Echinacea paradoxa* and *Echinacea* hybrids.

The new cultivar was selected from the results of the open pollination in 2007 in Hillegom, The Netherlands. Asexual reproduction of the new *Echinacea* by in vitro propagation in a controlled environment in Hillegom, The Netherlands since the summer of 2008, has shown that the unique features of the *Echinacea* are stable and reproduced true to type in successive generations.

SUMMARY OF THE INVENTION

The following are the most outstanding and distinguishing characteristics of this new cultivar when grown under normal horticultural practices in Hillegom, The Netherlands:

1. White-colored ray florets;
2. Floriferous;
3. Compact habit;
4. Healthy, abundant foliage; and
5. Good mildew resistance.

Of the many commercially available *Echinacea* cultivars, the most similar in comparison to the new cultivar is 'Matthew Saul', U.S. Plant Pat. No. 17,652. However, in side by side comparisons in Hillegom, The Netherlands, plants of the new cultivar 'White Mist' differ from plants of 'Matthew Saul' in at least the following characteristics:

1. Plants of the new cultivar are more floriferous than plants of 'Matthew Saul';
2. Plants of the new cultivar have a foliage color different from plants of 'Matthew Saul';
3. Plants of the new cultivar have a ray floret color different from plants of 'Matthew Saul'; and 4. Plants of the new cultivar have longer ray florets than plants of 'Matthew Saul'

In addition, plants of the new cultivar 'White Mist' are similar to 'Amber Mist', pending U.S. Plant patent application Ser. No. 12/592,652. However, in side by side comparisons in Hillegom, The Netherlands, plants of the new cultivar 'White Mist' differ from plants of 'Amber Mist' in flower color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'White Mist'. The plant was field grown for approximately 1 year in Hillegom, The Netherlands in an outdoor nursery location. Plants were transplanted into a one-gallon container for photography purposes.

DETAILED BOTANICAL DESCRIPTION

Figure 1:
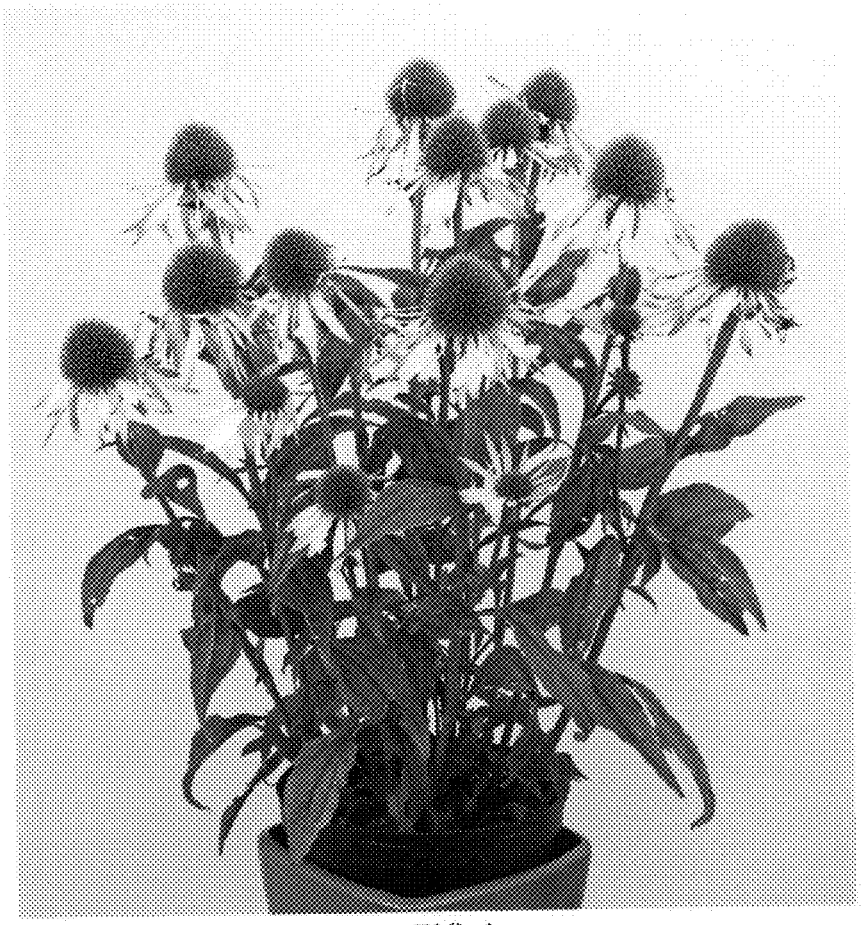
FIG. 1 illustrates a side view of the overall growth and flowering habit of 'White Mist'.
Figure 2:
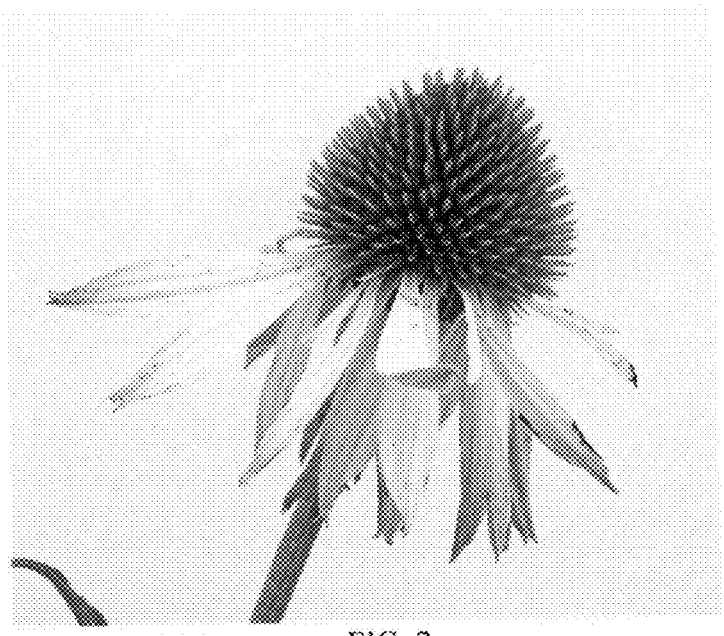
FIG. 2 illustrates a close-up view of an individual inflorescence of 'White Mist'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The data which define these characteristics were collected from asexual reproductions carried out in Hillegom, The Netherlands. The plant history was taken in August 2009 on 1-year-old field grown plants which were planted and grown outdoors in daytime temperatures between 14° C. and 28° C. and nighttime temperatures between 5° C. and 18° C. No pinching, growth retardants or photoperiodic treatments were used. Observations were made when the plants were in natural daylight conditions.

Botanical classification: *Echinacea hybrida* cultivar 'White Mist'.

Parentage:

*Female parent.*—Unknown *Echinacea* sp.

*Male parent.*—Unknown *Echinacea* sp.

Propagation:

*Type.*—In vitro propagation is preferred, divisions are possible.

*Time to initiate roots in vitro.*—Approximately 30 days at 14° C.

*Time to produce a rooted plantlet in summer.*—Approximately 30 days at 14° C.

*Root description.*—Fine, fibrous; grey in color.

*Rooting habit.*—Moderate density, poorly branched.

Plant description:

*Commercial crop time.*—Approximately 20 weeks from a rooted tissue culture plantlet to finish in a 1 gallon container.

*Growth habit and general appearance.*—Upright, narrow inverted triangle, herbaceous perennial.

*Growth rate.*—Moderately vigorous, approximately 17 cm per month in spring.

*Outdoor plant performance.*—Use as bedding plants or in mixed-container plantings; at least tolerant to temperatures up to 35° C. and hardy to USDA zone 4.

*Size.*—Height from soil level to top of plant plane: Approximately 49.1 cm. Width: Approximately 43.6 cm.

*Branching habit.*—No lateral branching, flowering stems grow from base. Quantity of main stems per plant: Approximately 14.

*Stems.*—Strength: Very strong. Aspect: Nearly erect, 5° angle from vertical. Shape: Rounded. Length to base of inflorescence: Approximately 34.8 cm. Diameter: Approximately 5.0 mm. Length of central internode: Approximately 5.2 cm. Texture: Moderately pubescent with short strigose hairs. Length of pubescence: Approximately 0.3 mm. Color of pubescence: 157D. Color of young and mature stems: 144A.

Foliage description:

*General description.*—Form: Simple. Arrangement: Alternate.

*Leaves.*—Aspect: Perpendicular to stem, subtending with age. Shape: Narrowly ovate, slightly carinate. Margin: Entire, very slightly undulate. Apex: Acute to long acute. Base: Attenuate. Venation pattern: Pinnate. Length of mature leaf: Approximately 10.4 cm. Width of mature leaf: Approximately 4.0 cm. Texture of upper and lower surfaces: Slightly glossy, moderately to densely pubescent with short strigose hairs. Length of pubescence: Approximately 0.3 mm. Color of pubescence: 157D. Color of upper surface of young foliage: 139A with 137A and venation of 144C. Color of lower surface of young foliage: 137B with venation of 144C. Color of upper surface of mature foliage: N137A with venation of 144C. Color of lower surface of mature foliage: 147B with venation of 144C.

*Petiole.*—Shape: V-shaped. Length: Approximately 2.1 cm. Diameter: Approximately 3.0 mm. Height: Approximately 4.0 mm. Texture of upper surface: Glabrous. Texture of lower surface: Glossy, sparsely covered with very short strigose hairs. Length of pubescence: Approximately 0.2 mm. Color of pubescence: Closest to 157D. Color of upper and lower surfaces: 144B.

Flowering description:

*Flowering habit.*—'White Mist' continuously flowers from early July to mid-September in The Netherlands.

*Lastingness of individual inflorescence on the plant.*—Approximately 14 days.

Inflorescence description:

*General description.*—Type: Solitary, composite. Persistent. Shape: Conical. Aspect: Facing upward. Arrangement: Terminal, held upright on strong peduncles. Fragrance: Faintly sweet. Quantity per plant: Approximately 14. Height: Approximately 7.5 cm. Diameter: Approximately 12.2 cm.

*Peduncle.*—Strength: Strong. Aspect: Erect. Length: Approximately 11.1 cm. Diameter: Approximately 5.0 mm. Texture: Moderately pubescent with short strigose hairs. Length of pubescence: Approximately 0.3 mm. Color of pubescence: 157D. Color: 144B.

*Bud.*—Quantity per plant: Approximately 3. Shape: Flattened globular with immature ray florets at approximately a 45° angle from horizontal. Length: Approximately 2.4 cm. Diameter: Approximately 3.7 cm. Color: 145A to 145B with a center of 143A to 144A.

*Ray florets.*—Quantity per inflorescence: Approximately 28. Arrangement: Imbricate in a single whorl. Aspect: Perpendicular to disc, subtending with age. Shape: Narrowly elliptic to linear. Appearance: Dull. Margin: Entire. Apex: Emarginate. Base: Cuneate. Length: Approximately 4.8 cm. Width: Approximately 7.0 mm. Texture of upper surface: Smooth, slightly ribbed longitudinally. Texture of lower surface: Smooth, ribbed longitudinally. Color of upper surface when first open: 155A with base of 145A to 145B. Color of lower surface when first open: 155A with base and tip of 145A to 145B. Color of upper surface when fully open: 157B to 157C with base of 145A to 145B. Color of lower surface when fully open: 145D with base and tip of 145A.

*Disc florets.*—Disc diameter: Approximately 4.4 cm. Quantity per inflorescence: Approximately 360. Arrangement: Spirally arranged in center of inflorescence. Shape: Tubular. Margin of free portion: Entire. Apex: Five acute tips. Base: Fused into a tube. Length: Approximately 1.0 cm. Diameter: Approximately 2.0 mm. Texture: Glabrous. Color of upper surface when first and fully open: 144A. Color of lower surface when first and fully open: 144B.

*Receptacle.*—Shape: Conical. Height: Approximately 1.8 cm. Diameter: Approximately 1.3 cm. Color: NN155B.

*Phyllaries.*—Quantity per inflorescence Approximately 48. Arrangement: In a three whorls. Appearance: Dull, stiff. Shape: Narrowly ovate to lanceolate, slightly curved towards the peduncle. Margin: Entire. Apex: Acute. Base: Cuneate. Length: Approximately 8.0 mm. Width: Approximately 2.5 mm. Texture of upper or inner surface: Glabrous. Texture of lower or outer surface: Glabrous with margins moderately to densely pubescent with short strigose hairs. Length of pubescence: Approximately 0.3 mm. Color of pubescence: 157D. Color of upper surface: 137B. Color of lower surface: 137A.

*Receptacle spines.*—Number of spines per disc: 360. Shape: Acicular. Apex: Acute. Base: Attenuate. Texture: Glabrous. Color: Apex of N25A with mid-section of 143B and base of 144D.

*Reproductive organs.*—Androecium: Present on disc florets only. Stamen quantity: 5 per floret. Anther shape: Oblong, basifixed. Anther length: Approximately 3.0 mm. Anther color: 200A to 202A. Filament length: Approximately 2.0 mm. Filament color: 145C. Pollen amount: Moderate to abundant. Pollen color: 17A. Gynoecium: Present on disc florets only. Pistil quantity: 1 per floret. Pistil length: Approximately 1.0 cm. Stigma shape: Decurrent. Stigma color: 151B to 151C. Style length: Approximately 6.0 mm. Style color: 151B. Ovary color: 145C to 145D.

Seed and fruit production: Neither seed nor fruit production has been observed.

Disease and pest resistance: Good mildew resistance. No particular resistance or susceptibility to other diseases or insects noted to date.

What is claimed is:

1. A new and distinct cultivar of *Echinacea* plant named 'White Mist', substantially as herein shown and described.

* * * * *